(12) United States Patent
Fulde (10) Patent No.: US 10,283,797 B2
(45) Date of Patent: May 7, 2019

(54) METHOD FOR STORING ELECTRIC ENERGY BY PRODUCTION, STORAGE, AND DISSOCIATION OF METHANE HAVING CLOSED CARBON CIRCUIT

(71) Applicant: Marek Fulde, Offenbach (DE)

(72) Inventor: Marek Fulde, Offenbach (DE)

( * ) Notice: Subject to any disclaimer, the term of this patent is extended or adjusted under 35 U.S.C. 154(b) by 267 days.

(21) Appl. No.: 15/021,544

(22) PCT Filed: Sep. 29, 2014

(86) PCT No.: PCT/EP2014/070758
§ 371 (c)(1),
(2) Date: Mar. 11, 2016

(87) PCT Pub. No.: WO2015/044407
PCT Pub. Date: Apr. 2, 2015

(65) Prior Publication Data
US 2016/0226088 A1   Aug. 4, 2016

(30) Foreign Application Priority Data

Sep. 30, 2013   (DE) .................... 10 2013 219 681

(51) Int. Cl.
*C01B 3/00* (2006.01)
*C01B 3/24* (2006.01)
(Continued)

(52) U.S. Cl.
CPC ......... *H01M 8/0656* (2013.01); *C01B 3/0021* (2013.01); *C01B 3/24* (2013.01);
(Continued)

(58) Field of Classification Search
CPC ......... H01M 8/02; H01M 8/0656; C01B 3/24; C01B 3/0021; C25B 15/08; C25B 1/04;
(Continued)

(56) References Cited

U.S. PATENT DOCUMENTS 3,904,386 A * 9/1975 Graboski .............. C07C 1/0485
423/656
2004/0148860 A1   8/2004 Fletcher
(Continued)

FOREIGN PATENT DOCUMENTS

DE   102007037672 A1   2/2009
DE   102012203334 A1   3/2012
(Continued)

OTHER PUBLICATIONS

Busse Karl-Hermann, Machine Translation of WO 2013/029701 A1, Mar. 2013 (Year: 2013).*
(Continued)

*Primary Examiner* — Sean P Cullen
(74) *Attorney, Agent, or Firm* — J.A. Lindeman & Co., PLLC (57) ABSTRACT

The invention relates to a method for storing electric energy, which comprises the steps
a) production of methane from water and soot using electric energy,
b) storage of the methane,
c) dissociation of the methane into hydrogen and soot, with the hydrogen being used for energy generation, or energy generation by conversion of the methane into soot and water in a cyclic bromination-oxidation process, wherein the soot formed in the dissociation of methane or in the cyclic bromination-oxidation process in step c) is collected and, in a renewed pass through the method, is used for methane production in step a), so that a closed carbon circuit is formed, and also a system comprising a power-methane conversion plant in which electric power is converted together with soot and water into methane and also a (Continued)

methane-power conversion plant in which methane is converted into hydrogen with elimination of soot.

10 Claims, 5 Drawing Sheets (51) Int. Cl.
*C07C 1/00* (2006.01)
*C25B 1/04* (2006.01)
*F02C 3/20* (2006.01)
*F02C 6/18* (2006.01)
*H01M 8/02* (2016.01)
*C25B 15/08* (2006.01)
*F01D 15/10* (2006.01)
*F01K 17/06* (2006.01)
*H02J 15/00* (2006.01)
*H01M 8/0656* (2016.01)

(52) U.S. Cl.
CPC .............. *C07C 1/00* (2013.01); *C25B 1/04* (2013.01); *C25B 15/08* (2013.01); *F01D 15/10* (2013.01); *F01K 17/06* (2013.01); *F02C 3/20* (2013.01); *F02C 6/18* (2013.01); *H01M 8/02* (2013.01); *C01B 2203/0272* (2013.01); *C01B 2203/0861* (2013.01); *C01B 2203/1241* (2013.01); *F05D 2220/32* (2013.01); *F05D 2220/72* (2013.01); *F05D 2220/76* (2013.01); *F05D 2240/35* (2013.01); *H02J 15/00* (2013.01); *Y02E 20/14* (2013.01); *Y02E 60/324* (2013.01); *Y02E 60/366* (2013.01); *Y02P 20/129* (2015.11); *Y02P 20/13* (2015.11); *Y02P 20/133* (2015.11); *Y02P 20/134* (2015.11); *Y02P 90/50* (2015.11)

(58) Field of Classification Search
CPC ... F02C 3/20; F02C 6/18; F01K 17/06; C01D 15/10; C07C 1/00

USPC ..................................... 429/416, 417; 60/698
See application file for complete search history.

(56) References Cited

U.S. PATENT DOCUMENTS

| | | | |
|---|---|---|---|
| 2009/0126271 A1* | 5/2009 | Kyo | C10J 3/463 48/77 |
| 2012/0091730 A1* | 4/2012 | Stuermer | C25B 1/04 290/1 R |
| 2013/0017460 A1* | 1/2013 | Keefer | B01D 53/047 429/419 |
| 2013/0023707 A1* | 1/2013 | Keefer | C01B 3/38 585/312 |
| 2015/0105923 A1 | 4/2015 | Beekmann | |
| 2015/0240716 A1 | 8/2015 | Dietrich | |

FOREIGN PATENT DOCUMENTS

| | | | |
|---|---|---|---|
| WO | 00/21911 A1 | 4/2000 | |
| WO | 2013/034130 A2 | 3/2013 | |
| WO | WO-2013029701 A1 * | 3/2013 | .............. C10G 2/50 |

OTHER PUBLICATIONS

Sterner, Michael, Bioenergy and renewable power methane in integrated 100% renewable energy systems, 2009, Kassel University Press (Year: 2009).*
International Preliminary Report on Patentability in corresponding International Application No. PCT/EP2014/070758, dated Mar. 31, 2016.
English abstract of DE 102007037672.
Europaische Kommission: EUR 17942 Aufbereitung der Kohle; Luxemburg, 1999.
English abstract of EUR 17942.

* cited by examiner

METHOD FOR STORING ELECTRIC ENERGY BY PRODUCTION, STORAGE, AND DISSOCIATION OF METHANE HAVING CLOSED CARBON CIRCUIT

The invention relates to a method for storing electric energy by converting electric energy into methane gas. The invention further relates to a system for storing electric energy.

Renewable energy sources such as photovoltaics or wind energy make it possible to generate energy, in particular electric power, without the emission of gases such as carbon dioxide ($CO_2$) which damage the climate. On the other hand, when fossil energy carriers such as oil, coal or natural gas are utilized, large amounts of damaging $CO_2$ are emitted. However, wind and sun are naturally not always available. Solar radiation is only available during the day. Furthermore, the availability of sun and wind energy depends on the weather conditions and the time of year. As a result, the consumption or energy requirement rarely matches energy production from renewable energies. According to planning to date, conventional power stations are therefore kept in reserve in order to compensate for a temporary undersupply of electric energy. Complete avoidance of $CO_2$ emissions is not possible in this way.

To achieve effective utilization of renewable energies, it is therefore of critical importance to store surplus electric energy in order to equalize peak loads and also an undersupply in the event of unfavorable weather conditions. However, stores which have been customary hitherto, e.g. pumped storage power stations, can store only small amounts of energy and suitable sites for the construction of further stores have been exhausted. New types of stores for electric energy are therefore the subject of numerous studies.

One possibility for storage is adiabatic compressed air stores in which compressors compress air in the event of an oversupply of electric energy and store it in subterranean caverns. The compressed air can then be used to drive turbines for power generation. However, a disadvantage is that the compressed air store can store only comparatively little electric energy. In addition, adiabatic compressed air stores are suitable only for short-term storage since the heat generated by compression of the air cannot be stored for any desired length of time.

The utilization of hydrogen from the electrolysis of water as storage medium has likewise been studied intensively. Hydrogen is suitable as emission-free fuel since it burns to form water. However, hydrogen can be transported only with difficulty, so that in the case of storage of electric energy the reconversion of the hydrogen should be carried out at the same place. However, it would be preferred to carry out the reconversion at the place at which the electric energy is required. Particularly in the case of offshore wind energy farms, the place where the energy is generated and the place where the energy is required are far apart, which imposes a severe load on the power grids.

A further possibility for storage is the production of methane gas. Here, methane gas is produced from hydrogen and carbon in a Sabatier reaction. For storage and transport, the methane gas can be introduced into the existing natural gas grid since methane is also the main constituent of natural gas. In this way, the energy could not only be stored but also be transported to the place at which the electric energy is required without additional loading of the power grids from the site at which the energy is generated.

DE-A 10 2007 037 672 discloses a method in which the energy generated from renewable sources is converted into hydrogen and subsequently converted together with $CO_2$ into methane. The $CO_2$ necessary for the reaction is separated off from the exhaust gases of power stations. The methane produced can subsequently be burned in a power station to generate power, with the $CO_2$ formed once again being separated off, so that a $CO_2$ circuit is formed.

A disadvantage of the prior art is, in particular, that firstly only part of the $CO_2$ formed can be separated off from the combustion exhaust gas, so that although the $CO_2$ emissions can be reduced, they cannot be completely avoided. Secondly, the separation and also handling of the gaseous $CO_2$ are complicated.

It is an object of the present invention to simplify the handling of carbon in the circuit and avoid $CO_2$ emissions.

A method for storing electric energy, which comprises the steps a) production of methane from water and soot using electric energy,
b) storage of the methane,
c) dissociation of the methane into hydrogen and soot, with the hydrogen being used for energy generation, wherein the soot formed in the dissociation of methane in step c) is collected and, in a renewed pass through the method, is used for methane production in step a), so that a closed carbon circuit is formed, is proposed.

As an alternative to the dissociation of the methane, energy generation can also be effected in step c) by conversion of the methane into soot and water in a cyclic bromination-oxidation process. In this case, the soot formed in the cyclic bromination-oxidation process is collected and, in a renewed pass through the method, used for methane production in step a). In this case, too, a closed carbon circuit is formed.

The carbon (soot) is thus not used as fuel for energy generation in the proposed method but instead serves as carrier for the hydrogen. The term energy generation is here intended to encompass both generation of electric power and also the use of the hydrogen obtained by dissociation of the methane in step c) for other energy uses such as heating, cooling or operation of transport means such as cars, goods vehicles, trains or ships. In particular, buildings can be heated or cooled by means of the energy generated.

The methane is preferably produced in a power-methane conversion plant with the aid of a Sabatier reaction. For this purpose, water ($H_2O$) is dissociated into hydrogen ($H_2$) and oxygen ($O_2$) by means of electrolysis in the first step a) of the method when electric energy is available. The water is heated to about 90° C., preferably by means of process steam, before the electrolysis. As an alternative, it is possible to employ high-temperature steam electrolysis (HotElly) in which the steam is dissociated into $H_2$ and $O_2$ at temperatures of from 900 to 1000° C. The electrolysis products hydrogen and oxygen are firstly stored in buffer vessels.

After sufficient amounts of hydrogen and oxygen for operation of a methanation plant have been produced, methanation is commenced. For this purpose, soot is taken from a store, predried in a dryer and converted together with the electrolysis products into methane.

As an alternative to methane production, it would also be possible to employ other hydrogenation reactions which make it possible to produce hydrocarbon compounds, e.g. the Fischer-Tropsch reaction. These materials, too, can be dissociated into hydrogen and soot by thermal dissociation.

In one variant of the method, the soot is, after drying, burned to form carbon dioxide ($CO_2$). Here, the oxygen formed in the electrolysis is preferably used. If the oxygen obtained is used in the combustion, the effectiveness of the method compared to the use of air is increased since there is then no need for separating off the nitrogen present in the air from the methane produced. The energy liberated in the form of heat during the combustion can be withdrawn from the $CO_2$ gas by means of a steam generator.

The steam can be used as process steam and/or for power generation. The hydrogen obtained in the electrolysis is added to the $CO_2$ produced, with a ratio of carbon dioxide to hydrogen which is optimal for the Sabatier reaction being set. A stoichiometric (1:4) to slightly superstoichiometric ratio based on hydrogen is optimal here. The gas mixture then flows into a hydrogenation plant where it is converted into methane over a catalyst at an elevated pressure in the range from about 8 to 30 bar (0.8 to 3.0 MPa), preferably in the range from about 8 to 10 bar. The heat liberated in the Sabatier reaction $CO_2 + 4H_2 = CH_4 + 2H_2O$ can likewise be withdrawn by means of a steam generator and utilized as process steam.

In a further embodiment of the method, the soot is, after drying, fed to a gasification plant. There, it is converted in the presence of oxygen and steam into synthesis gas at a temperature in the range from 900° C. to 1800° C., preferably from 1200 to 1800° C. The temperature in the reaction is particularly preferably about 1500° C. The heat liberated in the reaction of the soot to form synthesis gas can be withdrawn by means of a steam generator and utilized as process steam. The hydrogen from the electrolysis is subsequently added to the synthesis gas, with a ratio of carbon monoxide from the synthesis gas to hydrogen which is optimal for the hydrogenation reaction being set. A stoichiometric (1:3) to slightly superstoichiometric ratio based on hydrogen is optimal here. The gas mixture then flows into a hydrogenation plant where the synthesis gas is converted into methane over a catalyst in accordance with the reaction equation $CO + 3H_2 = CH_4 + H_2O$. Once again, the heat liberated in the hydrogenation reaction can be withdrawn by means of a steam generator and utilized as process steam.

In the above-described combustion or partial oxidation of the soot, relatively high temperatures of from 900° C. up to 1800° C. are achieved in order to avoid the production of harmful by-products such as tar or relatively long-chain hydrocarbons. The high enthalpy of the gas stream can be recovered by steam generation only with difficulty and with considerable losses. As an alternative, hydrogenation of soot by means of hydrogen with addition of steam is employed as preliminary stage for the methanation reaction. In this embodiment, soot, hydrogen and steam are introduced into a fluidized bed of solids. At temperatures in the range from 600-900° C. and a pressure in the range from 20 to 40 bar (2 to 4 MPa), a mixture of methane, carbon monoxide and carbon dioxide is formed. Since this reaction is endothermic, the bed of solids is brought to the operating temperature by combustion of the unreacted soot in a parallel reaction stage. Oxygen from the electrolysis of water is used for this purpose. Combustion gases are mixed into the methane/carbon oxide mixture and cooled to a temperature in the range from 200 to 250° C.

The heat which has been removed can be used for producing electric power. In the next reaction stage, the methanation of the remaining carbon oxides is carried out as in other examples of the method. Here too, the stoichiometric ratio is set by addition of the hydrogen obtained by electrolysis. The waste heat from the exothermic methanation reaction is utilized for power generation or as heat for district heating.

The methane produced can still contain residues of carbon dioxide. These are separated off in a carbon dioxide removal apparatus and fed back to the methanation reaction. Polyimide hollow fiber membranes can be used for separating off the carbon dioxide. The methane gas is then dried and compressed. Furthermore, the methane gas is adjusted so that the proportion of hydrogen ($H_2$) which is permissible for introduction into the gas grid is adhered to. The methane gas can subsequently be fed into the public natural gas grid for storage as per step b) of the method. As an alternative, it is also conceivable to store the methane gas in a pressure container.

When energy is required, the methane gas produced can be used for energy generation in a methane-power conversion plant as per step c) of the method. For this purpose, the methane gas is firstly preheated by means of process heat in a heat exchanger. The methane gas is subsequently fed to a plasma hydrogen generator. In the plasma hydrogen generator, dissociation of the methane into carbon (soot) and gaseous hydrogen is carried out. The plasma is generated, for example, by injection of microwaves. The plasma dissociation of methane takes place at relatively low temperatures in the range from about 400 to 600° C., so that thermal losses are minimized. In a filter installed downstream of the plasma hydrogen generator, the soot is separated from the hydrogen. The conversion of the methane into hydrogen and soot occurs with a yield of from about 96 to 97%. Other methods suitable for producing hydrogen from methane, for example the "channel black process" or the "Degussa black process" (also known to those skilled in the art as gas black Degussa process), can also be employed, although these operate at a lower effectiveness. In these methods, the methane gas is thermally dissociated. For this purpose, a methane gas/air mixture is fed to a burner consisting of a plurality of small burner hats.

The small flames formed there impinge against a water-cooled rotating roller where part of the soot is deposited. The remainder is separated off from the gas phase in a downstream filter plant. The further soot treatment or utilization of the air/hydrogen mixture is carried out analogously to the above-described plasma method.

As an alternative, a methane-power conversion plant which operates on the basis of a cyclic bromination-oxidation process can be used for generation of energy from the methane. The process comprises two exothermic reaction steps. In a first step, methane is reacted with bromine with elimination of soot to form hydrogen bromide. In a second step, hydrogen bromide is oxidized to water, with the bromine being liberated again and being reused.

The soot which has been separated off is agglomerated and cooled in a granulation apparatus. As granulation apparatus, it is possible to use, for example, a drum granulator. A downstream dryer dries the soot before it is stored in a store. From the store, the soot can subsequently be loaded onto a suitable transport means in order to be carried back to the power-methane conversion plant. The soot can then be used for the production of methane in a renewed pass through the method.

The hydrogen split off from the methane can then be utilized for energy generation. For this purpose, the hydrogen can be mixed with combustion air and burned in a gas turbine. The gas turbine drives an electricity generator by means of which electric power is produced. The exhaust gases from the combustion can be used in a steam generator for producing process steam. The process steam can then be utilized for drying the soot and/or for preheating the methane gas.

It is also conceivable to convert the hydrogen into electric power by means of a fuel cell, or to use the hydrogen for other purposes, for example for fueling hydrogen-powered vehicles or for heating.

In a preferred embodiment of the method, the power-methane conversion plant and the methane-power conversion plant are spatially separated from one another, with the methane being transported via the public gas grid. This makes it possible to produce the methane gas in the vicinity of the energy generators and carry out the conversion of the methane gas into electric power in the vicinity of the energy consumers.

In a further embodiment of the invention, heat arising in the production of methane in step a) of the method or in the energy generation in step c) of the method is at least partly fed into a district heating network.

The efficiency of the plants can be increased by utilization of the heat in the form of power-heat coupling.

The electric power required in the power-methane conversion is preferably generated from renewable resources. Electric power from wind power and solar plants is particularly suitable since in the case of these plants production is dependent on weather conditions and the time of year and does not match the demand of the energy consumers. Surplus energy which at present cannot be utilized by consumers can then be utilized for producing methane.

Furthermore, a system comprising a power-methane conversion plant, in which electric power is converted together with soot and water into methane, and a methane-power conversion plant, in which methane is converted with elimination of soot into hydrogen and subsequently into electric power, with means for recirculating the soot from the methane-power conversion plant to the power-methane conversion plant being provided, is proposed.

The methane-power conversion plant is for this purpose provided with facilities for the collection, agglomeration and drying of the soot. The soot is temporarily stored in a store and can from there be loaded into a transport means such as a goods vehicle or a railroad car. The power-methane conversion plant is provided with facilities for unloading the soot from the transport means into a store.

From the store, the soot can then be used for producing methane. Both the power-methane conversion plant and the methane-power conversion plant carry out the method described, so that the carbon is conveyed in a circuit. Here, the carbon is recirculated in solid form, which makes simple handling possible.

ADVANTAGES OF THE INVENTION

The method of the invention and the system of the invention do not use carbon as energy source but as carrier for hydrogen. The carbon is introduced once into the method and is subsequently circulated. Emissions of $CO_2$ or other climate-changing gases do not occur.

The hydrogen required for energy generation is obtained by means of power from renewable energy sources such as wind power and solar energy in the proposed method. These provide, even today, large quantities of electric energy when wind or sun is available, but these quantities frequently cannot be used or "consumed". This surplus energy can then be converted by means of the proposed method into methane, with the methane gas being stored in the public natural gas grid. The natural gas grid can take up large amounts of gas with only a small increase in pressure. Compared to simple storage of the energy carrier methane, the natural gas grid also allows transport over long distances, so that the conversion of methane gas back into electric power can be effected in the vicinity of the consumers. This considerably lightens the load on the power grids since a large part of renewable energies, e.g. from offshore wind power stations, is generated far away from the consumers of the energy.

If required, the stored energy can also be taken off in the form of hydrogen by means of the proposed method and this can, for example, be utilized for fueling hydrogen-powered vehicles.

Compared to the known methods for conversion and utilization of methane from renewable energies, the carbon is conveyed in a simple-to-handle circuit. The soot obtained in dissociation of methane can be separated off completely from the hydrogen and stored without a large outlay. The transport and handling of solid carbon are also less complicated than the handling of gaseous $CO_2$.

The invention will be described in more detail with the aid of the following drawings, the list of reference symbols and the claims.

THE FIGURES SHOW:

FIG. 1 a scheme of the method for storing electric energy,
FIG. 2 a scheme of a first embodiment of a power-methane conversion plant,
FIG. 3 a scheme of a second embodiment of a power-methane conversion plant,
FIG. 4 a scheme of a third embodiment of a power-methane conversion plant and
FIG. 5 a scheme of a methane-power conversion plant.

EMBODIMENTS OF THE INVENTION

In the following description of working examples of the invention, identical or similar components and elements are denoted by the same or similar reference symbols, with repeated description of these components or elements in individual cases being dispensed with. The figures depict the subject matter of the invention purely schematically.

Figure 1:
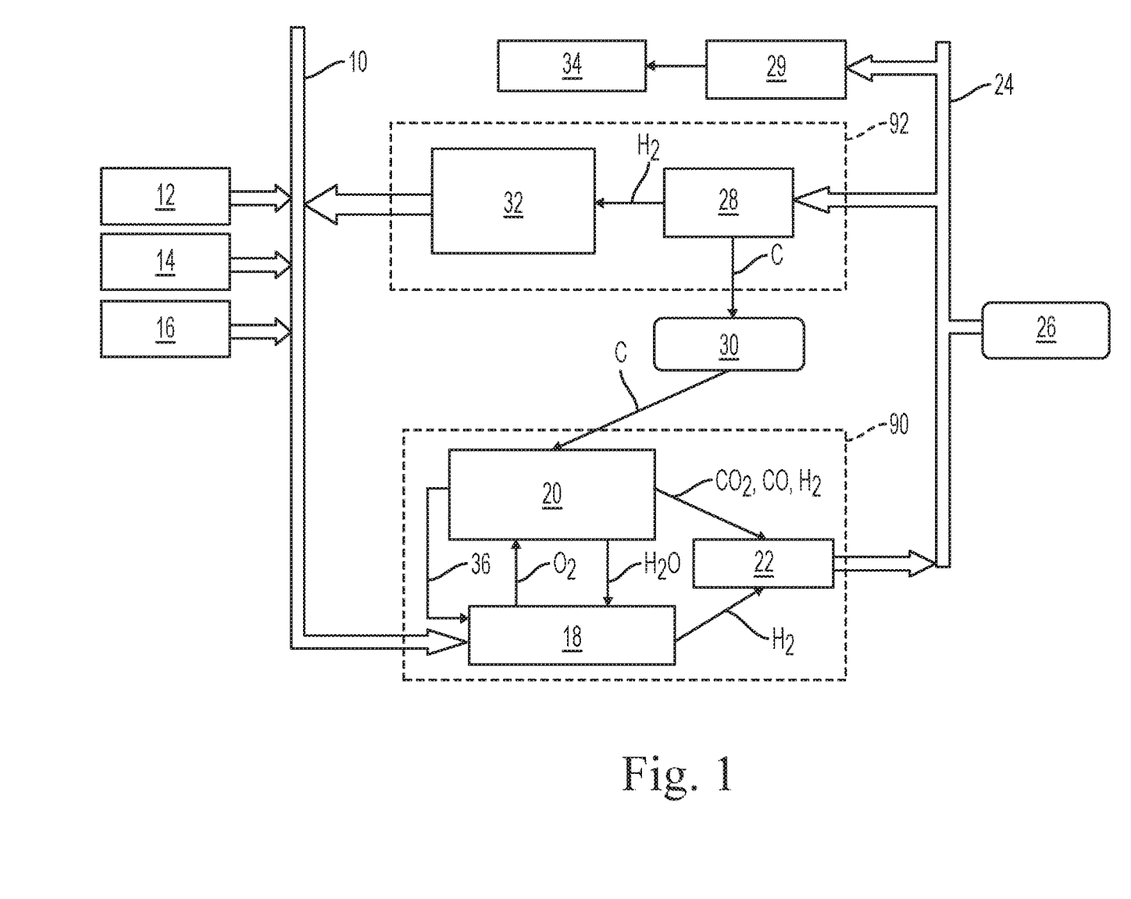

FIG. 1 shows a scheme of the proposed method for storing electric energy.

FIG. 1 schematically shows a power-methane conversion plant 90 and a methane-power conversion plant 92. The power-methane conversion plant 90 takes electric energy from the power grid 10 when there is a surplus of electric power from renewable energy sources. The renewable energy can be, in particular, wind energy 12 or solar energy 14, but can also originate from other sources 16 such as hydroelectric power.

The electric power is utilized in the power-methane conversion plant 90 to dissociate water $H_2O$ into hydrogen $H_2$ and oxygen $O_2$ by means of electrolysis 18. The oxygen $O_2$ is reacted with soot C from a soot store 30 and water in a coal gasification unit 20 to give synthesis gas containing carbon dioxide $CO_2$, carbon monoxide CO and hydrogen $H_2$. As an alternative, it is possible to burn the soot C from the soot store 30 with introduction of oxygen $O_2$ to form $CO_2$. Both the combustion and the reaction to form synthesis gas liberate heat which is utilized for preheating the water $H_2O$ which is fed to the electrolysis 18. Likewise, the heat can be used for power generation, with the electric power produced likewise being able to be utilized, via a power line 36, for the electrolysis 18.

The synthesis gas or carbon dioxide formed in the coal gasification unit 20 is subsequently introduced together with the hydrogen $H_2$ from the electrolysis 18 into the methanation 22. There, methane gas is produced in a Sabatier reaction or a hydrogenation reaction. This is compressed and, after being freed of remaining carbon dioxide, fed into the public gas grid 24 which serves as gas store 26.

When electric energy is required because no wind energy 12 or solar energy 14 is available at the time, methane gas is taken from the gas grid 24 and fed into the methane-power conversion plant 92. There, the methane gas is dissociated into hydrogen $H_2$ and soot C by means of a hydrogen generator 28. The soot C is introduced into the store 30 where it is available for renewed conversion into methane. The hydrogen $H_2$ from the hydrogen generator 28 is then supplied to a gas power station 32 which burns the hydrogen and generates electric power. The electric power generated is then again fed into the power grid 10.

As an alternative or in addition, hydrogen 34 for fueling hydrogen-powered vehicles or for other purposes, for example for heating, can be produced by means of a further hydrogen generator 29.

The carbon used is circulated in its entirety, being transported in solid form between the methane-power conversion plant 92, the carbon store 30 and the power-methane conversion plant 90. Complicated separation of carbon dioxide from combustion exhaust gases and transport of gaseous carbon dioxide are thus avoided.

Figure 2:
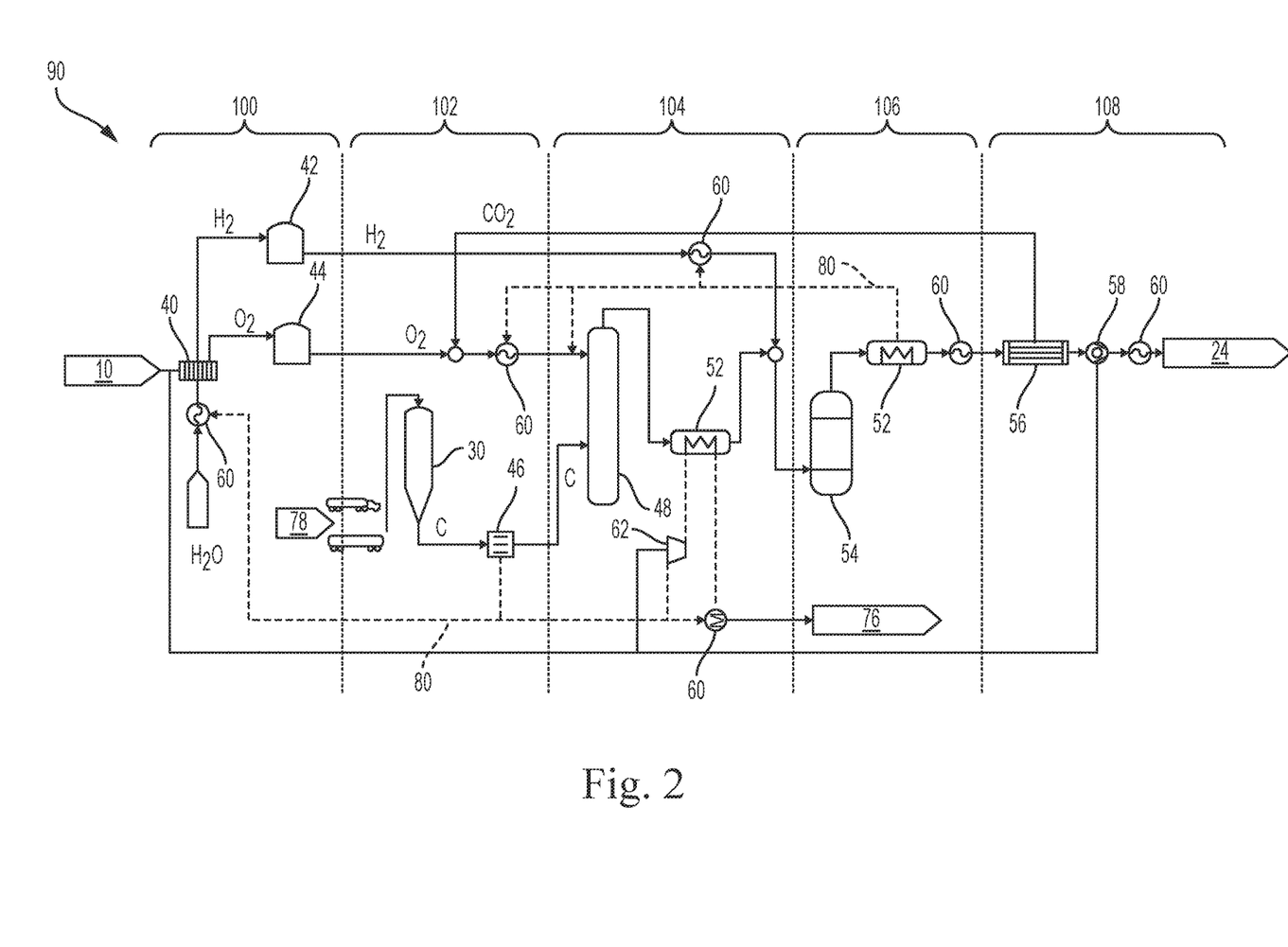

FIG. 2 shows a scheme of a first embodiment of a power-methane conversion plant.

FIG. 2 schematically shows a power-methane conversion plant 90. The plant comprises five sections. In the first section 100, the electrolysis is carried out. Electric power is taken from the power grid 10 and supplied to a water electrolyzer 40. The electrolyzer 40 dissociates water $H_2O$, which is heated to about 90° C. by means of process steam in a heat exchanger 60, into hydrogen $H_2$ and oxygen $O_2$. The electrolysis products are each temporarily stored in a hydrogen container 42 and an oxygen container 44. When sufficient amounts of hydrogen and oxygen are present, methane production is commenced.

For this purpose, soot C is taken at a supply point 78 and introduced into a carbon store 30 in the second section 102. The soot C is taken from the carbon store 30 and fed to a dryer 46. The soot C is introduced together with oxygen $O_2$ from the oxygen container 44 into a carbon gasification unit 48. The oxygen is preheated by means of a heat exchanger 60 in the second section 102.

In the third section 104, the soot is converted into synthesis gas. The soot and the preheated oxygen react in the presence of steam at a temperature in the range from 900 to 1800° C., preferably from 1200 to 1800° C., in the carbon gasification unit 48 to form synthesis gas. The temperature in the reaction is particularly preferably about 1500° C. The heat liberated in the reaction of the soot to form synthesis gas can be withdrawn by means of a steam generator 52 and utilized as process steam. In the embodiment shown in FIG. 2, the process stream is conveyed via a heat line 80 to a heat exchanger 60 which heats water before entry into the electrolyzer 40. It is likewise possible to use part of the process stream for power generation in a power generator 62. The electric power generated can be fed into the power grid 10 and used for electrolysis.

After gasification of the carbon, hydrogen from the electrolysis is added to the synthesis gas, with a ratio of carbon monoxide from the synthesis gas and hydrogen which is optimal for the hydrogenation reaction being set. Here, a stoichiometric (1:3) to slightly superstoichiometric ratio based on hydrogen is optimal.

The gas mixture then flows into a hydrogenation plant 54 in the fourth section 106, where the synthesis gas is converted over a catalyst into methane according to the reaction $CO+3H_2=CH_4+H_2O$. Once again, the heat liberated in the hydrogenation reaction can be withdrawn by means of a steam generator 52 and utilized as process steam. In the embodiment depicted, the heat is conveyed via a heat line 80 to a heat exchanger 60 which heats the oxygen before entry into the carbon gasification unit 48. A further heat exchanger 60 preheats the hydrogen before mixing with the synthesis gas. The methane gas is cooled by means of a heat exchanger 60.

In the last section 108, the methane gas is passed through a carbon dioxide removal 56. In the carbon dioxide removal 56, $CO_2$ remaining in the methane gas is separated off, for example by means of polyimide hollow fiber membranes, and recirculated to the methanation process. The $CO_2$ is fed together with the oxygen $O_2$ back to the carbon gasification unit 48. The methane gas is subsequently compressed by means of a methane compressor 58. Heat generated here is removed by means of a further heat exchanger 60 before the methane gas is fed into the public gas grid 24. Here, the gas grid 24 serves firstly as transport medium and secondly as gas store.

Process heat which is not required for preheating the water, the hydrogen or the oxygen can be fed via a further heat exchanger 60 into a district heating network 76 and utilized further.

Figure 3:
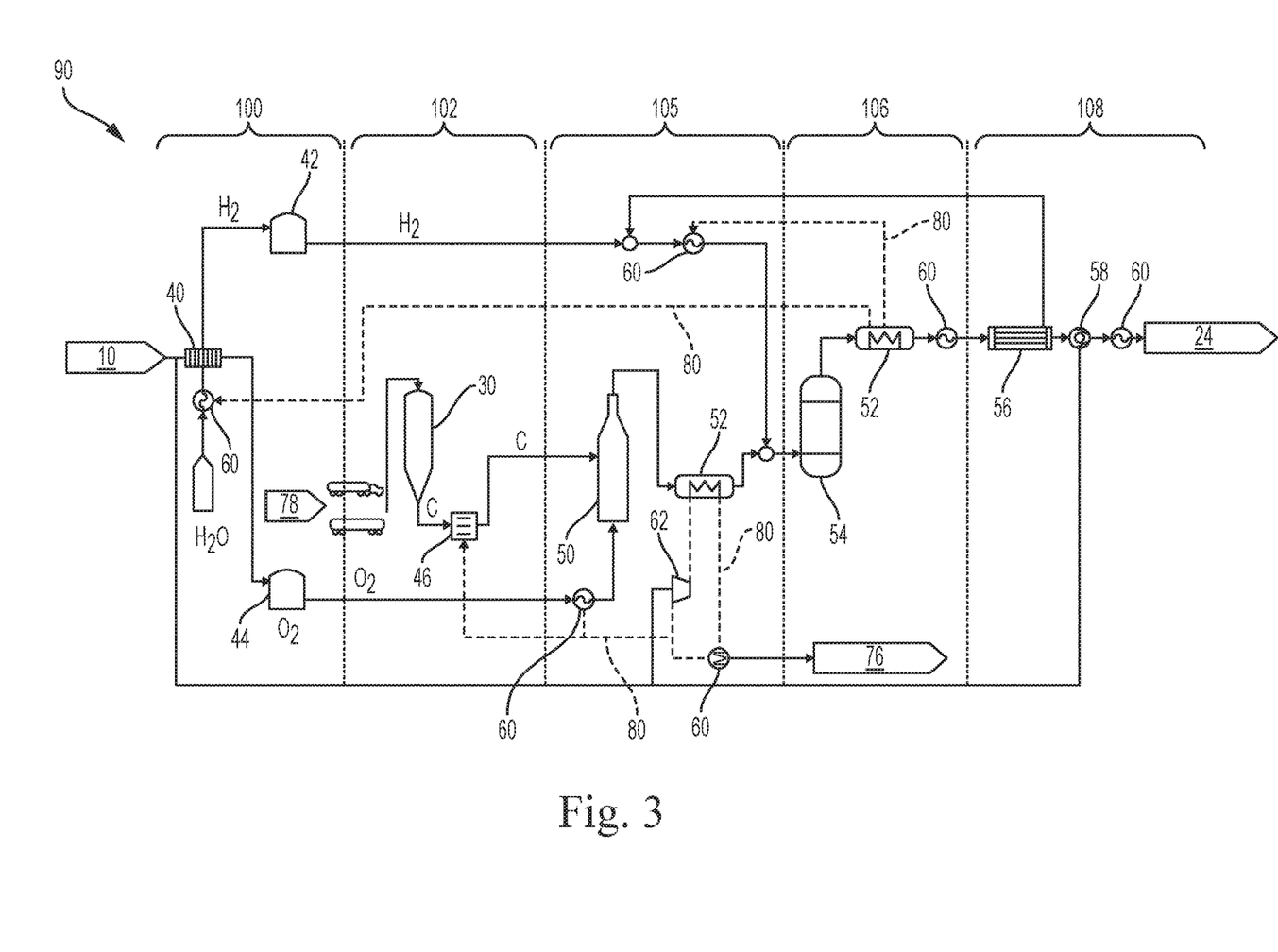

FIG. 3 shows a scheme of a further embodiment of a power-methane conversion plant.

FIG. 3 schematically shows a second embodiment of a power-methane conversion plant 90. The plant once again comprises five sections. In the first section 100, the electrolysis is carried out. Electric power is taken from the power grid 10 and supplied to a water electrolyzer 40. The electrolyzer 40 dissociates water $H_2O$, which is preheated to about 90° C. by means of process steam in a heat exchanger 60, into hydrogen $H_2$ and oxygen $O_2$. The electrolysis products are each temporarily stored in a hydrogen container 42 and an oxygen container 44.

When sufficient amounts of hydrogen and oxygen are present, methane production is commenced.

For this purpose, soot C is taken at a supply point 78 and introduced into a carbon store 30 in the second section 102. The soot C is taken from the carbon store 30 and fed to a dryer 46. The soot C is introduced together with oxygen $O_2$ from the oxygen container 44 into a carbon combustion unit 50.

In the third section 105, the soot is burned together with the oxygen $O_2$ from the electrolysis to form carbon dioxide $CO_2$. The oxygen is preheated by means of a heat exchanger 60. The heat liberated in the combustion of the soot C can be withdrawn by means of a steam generator 52 and utilized as process steam. The process steam can be conveyed via a heat line 80 to the soot dryer 46. It is likewise possible to use part of the process steam for power generation in a power generator 62. The electric power generated can be fed into the power grid 10 and used for the electrolysis.

In the fourth section 106, the hydrogen obtained in the electrolysis is then added to the $CO_2$ produced, with a ratio of carbon dioxide to hydrogen which is optimal for the Sabatier reaction being set. A stoichiometric (1:4) to slightly superstoichiometric ratio based on hydrogen is optimal. The gas mixture then flows into a hydrogenation plant 54 where it is converted over a catalyst into methane. The heat liberated in the Sabatier reaction $CO_2+4H_2=CH_4+2H_2O$ can likewise be withdrawn by means of a steam generator 52 and utilized as process steam. In the embodiment shown in FIG. 3, the process steam is conveyed via a heat line 80 to the heat exchanger 60 in order to preheat water before entry into the electrolyzer 40. Before being mixed with the carbon dioxide, the hydrogen is heated by means of a further heat exchanger 60.

In the last section 108 the methane gas is passed through a carbon dioxide removal 56. In the carbon dioxide removal 56, $CO_2$ remaining in the methane gas is separated off, for example by means of polyimide hollow fiber membranes, and recirculated to the methanation process. The $CO_2$ is conveyed together with the hydrogen $H_2$ from the electrolysis back to the hydrogenation plant 54. The methane gas is subsequently compressed by means of a methane compressor 58. Heat generated here is removed by means of a further heat exchanger 60 before the methane gas is fed into the public gas grid 24.

Process heat which is not required for preheating the water, the hydrogen or the oxygen can be fed via a further heat exchanger 60 into a district heating network 76 and utilized further.

Figure 4:
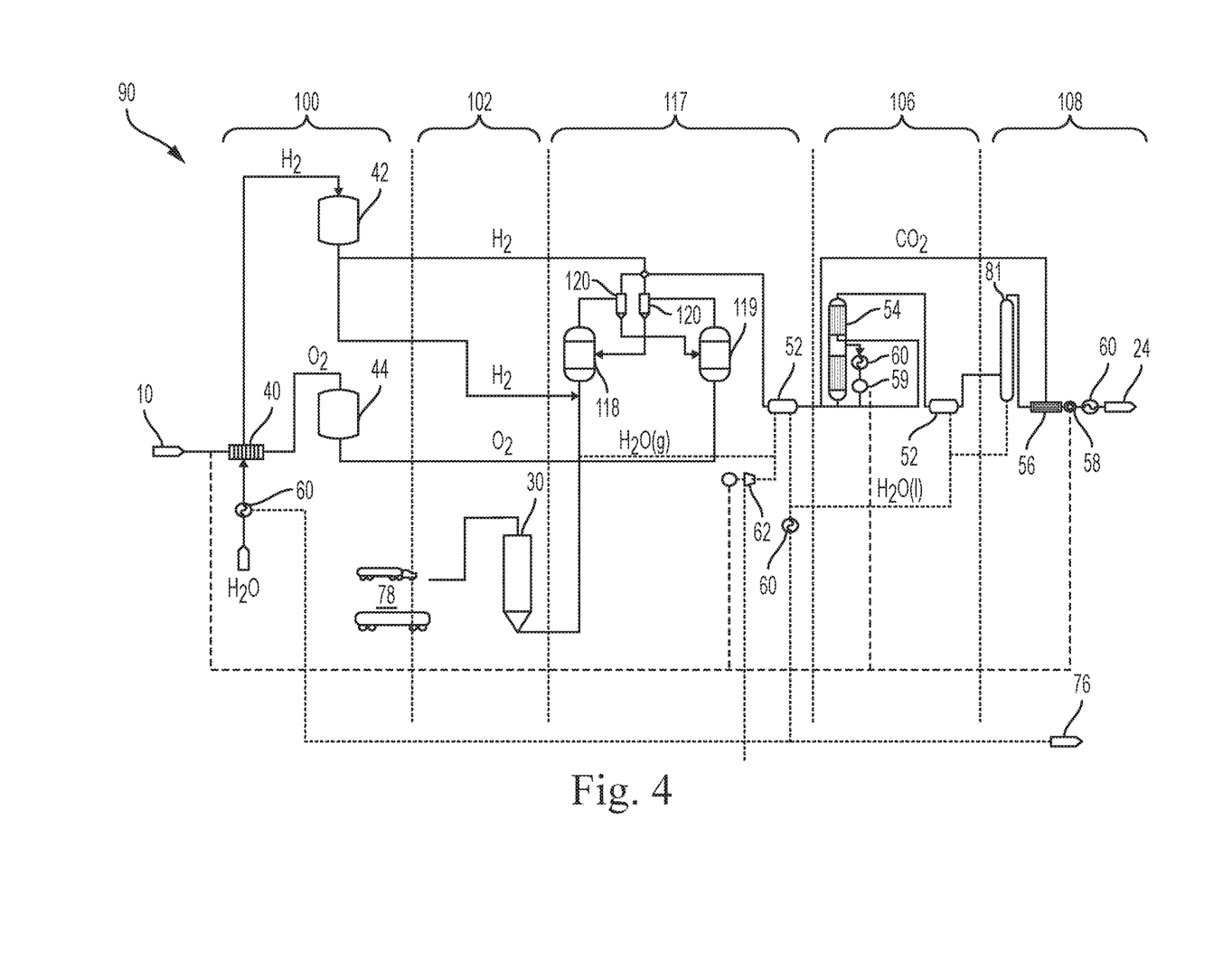

FIG. 4 shows a scheme of a third embodiment of a power-methane conversion plant.

The power-methane conversion plant 90 shown schematically in FIG. 4 can, as in the two previous embodiments, be divided into five sections. In the first section 100, the electrolysis is carried out. The operating parameters and technical configuration are the same as in the two above-described working examples.

The storage facility for soot is shown in section 102. Soot C is taken at a supply point 78 and introduced into a carbon store 30. From there, the soot C is taken off and transported to a hydrogasification plant 118. Drying of the soot C is not necessary.

In the third section 117, soot is conveyed together with hydrogen and steam to the hydrogasification plant 118. Sand which has been preheated to a temperature in the range from 700 to 800° C. is fluidized there by means of the gas mixture. The sand represents a bed of solids. A pressure in the range from 2.0 to 3.0 MPa (20 to 30 bar) prevails in the apparatus. The $H_2/H_2O$/soot mixture is converted into methane $CH_4$ and carbon dioxide $CO_2$. The ratio of the products $CH_4$:$CO_2$ is about 1:1. The product gases and part of the sand bed are discharged from the apparatus. Sand is separated off in the cyclone 120 and fed to the regenerator 119. Since soot is not completely reacted in the hydrogasification plant 118, it is conveyed together with sand to the regenerator 119. In the regenerator 119, the soot is burned in the presence of oxygen from the oxygen container 44. Sand is likewise fluidized here. Regenerated sand is separated off in a further cyclone 120 and returned to the hydrogasification plant 118.

The combustion gases are mixed with reaction products and additional hydrogen from the hydrogen container 42, so that an optimal ratio of carbon dioxide to hydrogen of 1:4 is set. The mixture is cooled to the optimal temperature for the subsequent methanation. In this embodiment, the waste heat is used for steam generation and generation of electric power. Electric power is employed internally for operation of the compressors 58 and also for the water electrolysis 40.

In the fourth section 106, the conversion of the carbon dioxide into methane over a catalyst is carried out in a hydrogenation plant 54. The catalyst can be divided into a plurality of, for example two, sections. The heat of reaction is removed between the sections in order to increase the yield. As an alternative, a reactor cascade can be used for the same purpose. Part of the reaction gas mixture is for this purpose circulated by means of a blower 59. The steam $H_2O$ (g) produced in the downstream steam generator 52 is converted into electric power and utilized for the electrolysis in the electrolyzer 40.

In the last section 108, water $H_2O$ (l) is firstly separated off from the gas mixture by condensation in a separator 81. As described above in respect of the first and second embodiments, the methane gas is subsequently prepared for introduction into the public gas grid 24.

Figure 5:
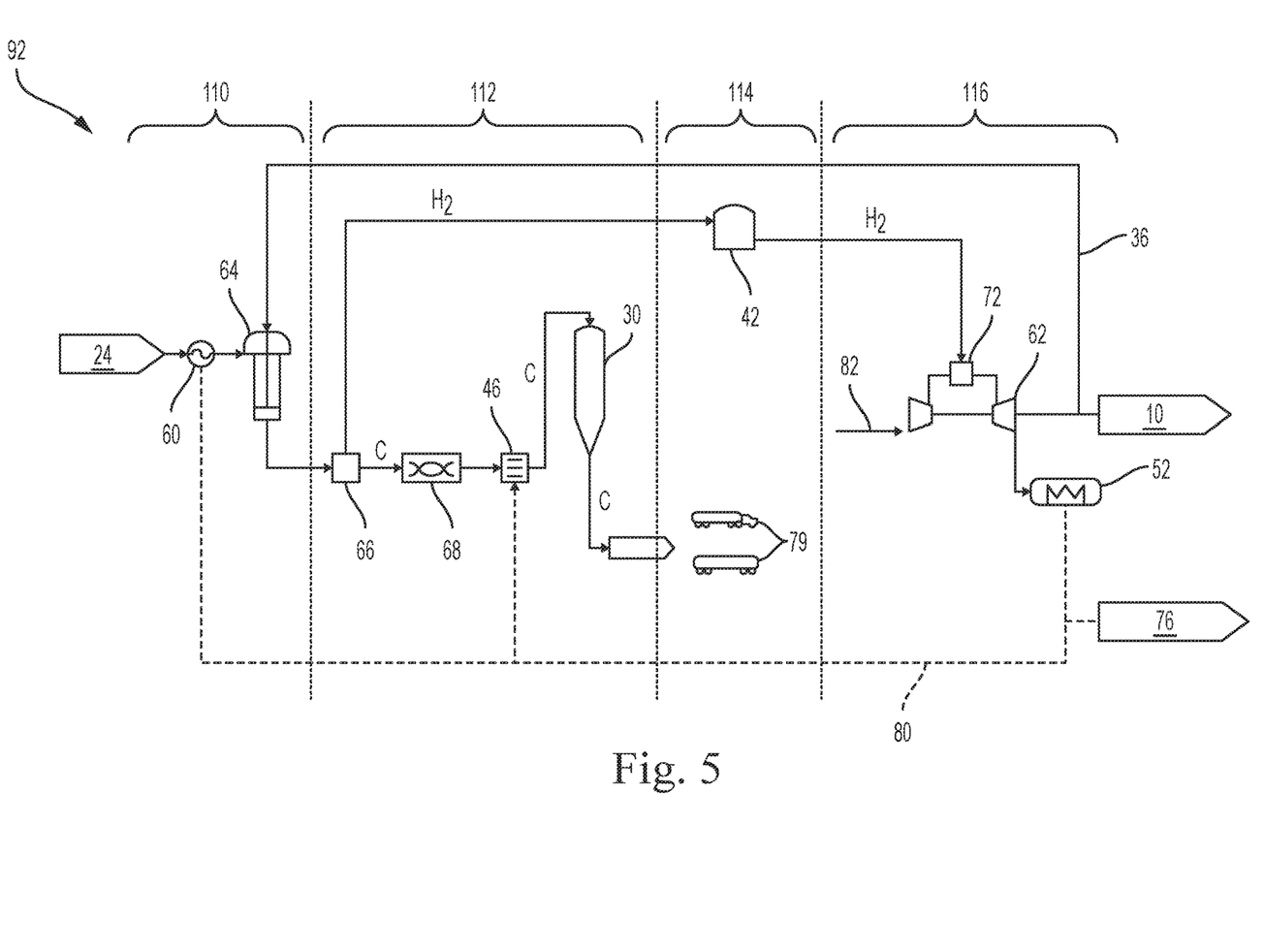

FIG. 5 shows a scheme of a methane-power conversion plant.

A methane-power conversion plant 92 is shown in FIG. 5. In the first section 110 of the plant, methane gas is taken from the gas grid 24. The methane gas is preheated by means of a heat exchanger 60 and subsequently introduced into a plasma hydrogen generator 64. There, a plasma is generated by means of microwave radiation and dissociates the methane gas into carbon (soot) and hydrogen $H_2$ at a temperature in the range from about 400 to 600° C.

Hydrogen and carbon are taken off from the plasma hydrogen generator 64 and separated from one another at a soot filter 66 in the second section 112. The soot is agglomerated in a granulation device 68. This can, for example, be configured as a drum granulator. The soot is subsequently dried in a dryer 46 before being transported into a carbon store 30. From there, the soot can be loaded by means of a loading facility 79 into a suitable transport container and transported away. The return transport to the power-methane conversion plant can, for example, be effected by means of goods vehicles or railroad cars.

The hydrogen which has been separated off is temporarily stored in a hydrogen container 42 in the third section 114 before being converted into electric power in the fourth section 116. For this purpose, the hydrogen $H_2$ is mixed with air 82 and subsequently burned in a hydrogen turbine 72. A power generator 62 generates electric power from the hot combustion exhaust gases and this power can be fed into the power grid 10. Part of the electric energy generated is required by the conversion plant itself for operation of the plasma hydrogen generator 64 and is conveyed via the power line 36.

The heat obtained in the combustion of the hydrogen can be utilized as process heat in a steam generator 52. The steam generated can then be utilized via a heat line 80 for, for example, preheating the methane gas. It is likewise possible to feed part of the heat into a district heating network 76.

As an alternative, it is also possible to use a methane-power conversion plant which operates on the basis of a cyclic bromination-oxidation process. Here, heat is firstly generated by means of the cyclic bromination-oxidation process. This heat can be used for power generation and/or fed into a district heating network.

In a further embodiment, a thermal process, e.g. the gas black Degussa process, can be used instead of the plasma process for dissociating the methane.

The invention is not restricted to the working examples described here and the aspects emphasized therein. Rather, many modifications which are a matter of routine for a person skilled in the art are possible within the scope defined by the claims.

The invention claimed is:

1. A method for the production of methane using electric energy and subsequent energy generation, which comprises the steps
    a) production of methane from water and soot using electric energy,
    b) storage of the methane, c) dissociation of the methane into hydrogen and soot, with the hydrogen being used for energy generation or, energy generation by conversion of the methane into soot and water in a cyclic bromination-oxidation process, characterized in that the soot formed in the dissociation of methane or in the cyclic bromination-oxidation process in step c) is collected and, in a renewed pass through the method, is used for methane production in step a), so that a closed carbon circuit is formed.

2. The method as claimed claim 1, characterized in that the storage of the methane is effected by feeding into a gas grid.

3. The method as claimed in claim 1, characterized in that the dissociation of the methane and the energy generation according to step c) are carried out at a different place than the production of the methane according to step a).

4. The method as claimed in claim 1, wherein, for the energy generation according to step c) of the method, the hydrogen obtained is (1) converted in a fuel cell into electric energy, (2) used for heating, (3) used for cooling, (4) used as fuel for transport, or a combination of any one of (1) to (4).

5. The method as claimed in claim 1, characterized in that heat arising in the production of methane according to step a) and/or in the energy generation according to step c) is fed into a district heating network.

6. The method as claimed in claim 1, characterized in that the electric energy used in step a) is generated using renewable resources.

7. The method as claimed in claim 6, characterized in that the electric energy is generated by wind power or a solar plant.

8. The method as claimed in claim 1, characterized in that the step of production of the methane is carried out by a Sabatier reaction or by a hydrogenation reaction.

9. The method as claimed in claim 8, characterized in that the hydrogen, which is required in the Sabatier reaction or in the hydrogenation reaction, is obtained from water by electrolysis.

10. The method as claimed in claim 8, characterized in that the soot for carrying out the Sabatier reaction is burnt to form carbon dioxide or the soot is converted in the presence of oxygen and steam into synthesis gas, with the oxygen being obtained by electrolysis of water.

\* \* \* \* \*